(12) United States Patent
Kyle et al.

(10) Patent No.: US 12,005,834 B2
(45) Date of Patent: Jun. 11, 2024

(54) AUTONOMOUS SEAT SANITIZING SYSTEM FOR A VEHICLE

(71) Applicant: Toyota Motor North America, Inc., Plano, TX (US)

(72) Inventors: Roger Akira Kyle, Frisco, TX (US); Timothy Wang, Ypsilanti, MI (US); Bryan E. Yamasaki, Ypsilanti, MI (US)

(73) Assignee: Toyota Motor North America, Inc., Plano, TX (US)

( * ) Notice: Subject to any disclaimer, the term of this patent is extended or adjusted under 35 U.S.C. 154(b) by 647 days.

(21) Appl. No.: 17/029,854

(22) Filed: Sep. 23, 2020

(65) Prior Publication Data

US 2022/0088249 A1    Mar. 24, 2022

(51) Int. Cl.

| | |
|---|---|
| *A61L 2/24* | (2006.01) |
| *A61L 2/10* | (2006.01) |
| *B60Q 1/00* | (2006.01) |
| *B60Q 3/217* | (2017.01) |
| *B60Q 3/233* | (2017.01) |
| *B60Q 3/70* | (2017.01) |

(52) U.S. Cl.
CPC ............... *B60Q 3/217* (2017.02); *A61L 2/10* (2013.01); *A61L 2/24* (2013.01); *B60Q 1/0023* (2013.01); *B60Q 3/233* (2017.02); *B60Q 3/70* (2017.02); *A61L 2202/14* (2013.01); *A61L 2202/25* (2013.01)

(58) Field of Classification Search
CPC .......... A61L 2/24; A61L 2/10; A61L 2202/14; A61L 2202/25; A61L 2202/11; B60Q 1/0023; B60Q 3/233; B60Q 3/68; B60Q 3/70; B60Q 3/217; B60N 2/002
See application file for complete search history.

(56) References Cited

U.S. PATENT DOCUMENTS

| | | | |
|---|---|---|---|
| 8,114,346 | B2 | 2/2012 | Hyde et al. |
| 9,511,159 | B2 | 12/2016 | Kreiner et al. |
| 9,694,739 | B2 | 7/2017 | Salter et al. |
| 9,782,504 | B2 | 10/2017 | Holub et al. |

(Continued)

FOREIGN PATENT DOCUMENTS

| | | |
|---|---|---|
| KR | 20160069827 A | 6/2016 |
| WO | 2017042095 A1 | 3/2017 |

*Primary Examiner* — Regina M Yoo
(74) *Attorney, Agent, or Firm* — Christopher G. Darrow; Darrow Mustafa PC

(57) ABSTRACT

An autonomous seat sanitizing system for a vehicle includes a vehicle seat sanitizing system control module configured to detect a person approaching a vehicle. Responsive to a person approaching the vehicle, a distance of the person from the vehicle is determined. The distance of the person from the vehicle is compared to a predetermined threshold distance. If the distance of the person from the vehicle is less than the predetermined threshold distance, the control module determines if at least one seat in the vehicle occupant compartment is unoccupied. If at least one seat is unoccupied, the module controls operation of the vehicle to direct a sanitizing ultraviolet (UV) light onto the unoccupied seat until a vehicle door is opened from an exterior of the vehicle, or until the distance of the person from the vehicle is no longer less than the predetermined threshold distance.

10 Claims, 6 Drawing Sheets

(56) References Cited

U.S. PATENT DOCUMENTS

| | | | |
|---|---|---|---|
| 2013/0145692 A1* | 6/2013 | Laird | E05F 15/73 49/31 |
| 2014/0316607 A1* | 10/2014 | Le | B60N 2/0248 701/1 |
| 2014/0316660 A1* | 10/2014 | Le | B60N 2/0248 701/49 |
| 2015/0190538 A1 | 7/2015 | Olvera et al. | |
| 2018/0369434 A1 | 12/2018 | Callahan | |
| 2019/0076558 A1 | 3/2019 | Zhang-Miske et al. | |
| 2019/0091738 A1† | 3/2019 | Chen | |
| 2020/0061223 A1 | 2/2020 | Hallack | |

\* cited by examiner
† cited by third party

AUTONOMOUS SEAT SANITIZING SYSTEM FOR A VEHICLE

TECHNICAL FIELD

The subject matter described herein relates to sanitizing systems and, more particularly, to a system for autonomously sanitizing vehicle seats before and/or after use.

BACKGROUND

It is increasingly important for both medical and psychological reasons for people to feel that surfaces they touch will be sanitized to cleanse bacteria and viruses from the surfaces. Numerous users may sit in the various seats of a passenger vehicle. These seats may be rarely sanitized after use, and it may be burdensome for vehicle owners to manually spray or wipe-down the seats before and/or after every use.

SUMMARY

In one aspect of the embodiments described herein, an autonomous seat sanitizing system for a vehicle is provided. The system includes one or more processors and a memory communicably coupled to the one or more processors. The memory stores a vehicle seat sanitizing system control module configured to detect a person approaching a vehicle. Responsive to detection of the person approaching the vehicle, a distance of the person from the vehicle is determined and constantly updated. The distance of the person from the vehicle is compared to a predetermined threshold distance. If the distance of the person from the vehicle is less than the predetermined threshold distance, the vehicle seat sanitizing system control module determines if at least one seat in the vehicle occupant compartment is unoccupied. If at least one seat in the vehicle occupant compartment is unoccupied, the module controls operation of the vehicle to direct a sanitizing ultraviolet (UV) light onto the at least one unoccupied seat until a vehicle door is opened from an exterior of the vehicle, or until the distance of the person from the vehicle is no longer less than the predetermined threshold distance.

BRIEF DESCRIPTION OF THE DRAWINGS

The accompanying drawings, which are incorporated in and constitute a part of the specification, illustrate various systems, methods, and other embodiments of the disclosure. It will be appreciated that the illustrated element boundaries (e.g., boxes, groups of boxes, or other shapes) in the figures represent one embodiment of the boundaries. In some embodiments, one element may be designed as multiple elements or multiple elements may be designed as one element. In some embodiments, an element shown as an internal component of another element may be implemented as an external component and vice versa. Furthermore, elements may not be drawn to scale.

DETAILED DESCRIPTION

Embodiments described herein relate to an autonomous seat sanitizing system for a vehicle. The system may provide several operational modes designed to sanitize one or more unoccupied vehicle seats with a UV light, either prior to a user occupying the seat(s) or after user(s) have vacated the seat(s). In one exemplary operational mode. The system may be configured to detect a person approaching a vehicle. Responsive to detection of the person approaching the vehicle, a distance of the person from the vehicle is determined and constantly updated. The distance of the person from the vehicle is compared to a predetermined threshold distance. If the distance of the person from the vehicle is less than the predetermined threshold distance, the vehicle seat sanitizing system control module determines if at least one seat in the vehicle occupant compartment is unoccupied. If at least one seat in the vehicle occupant compartment is unoccupied, the module controls operation of the vehicle to direct a sanitizing ultraviolet (UV) light onto the at least one unoccupied seat until a vehicle door is opened from an exterior of the vehicle, or until the distance of the person from the vehicle is no longer less than the predetermined threshold distance. Other operational modes are also described.

Figure 1:
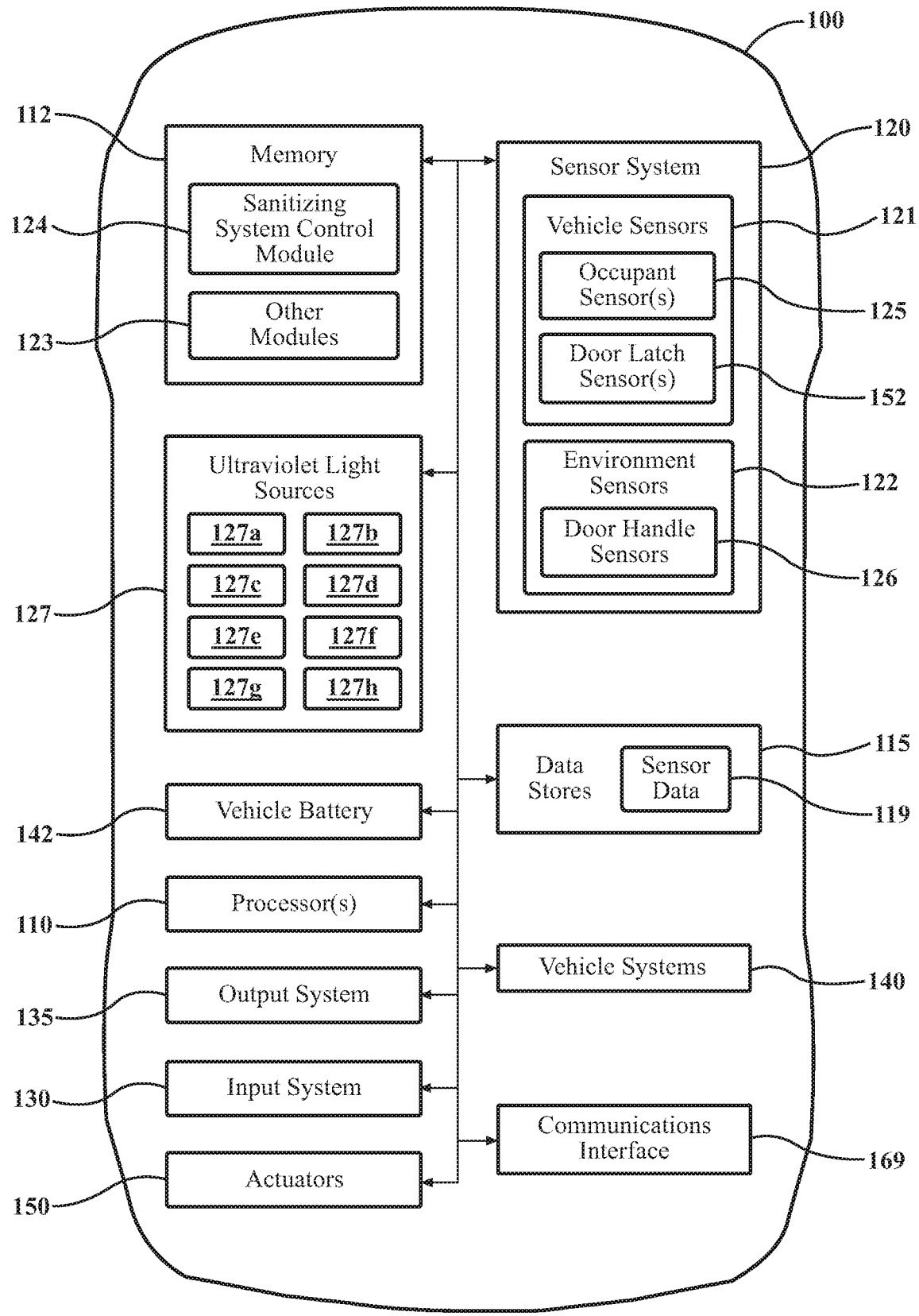
FIG. 1 is a block schematic diagram of a vehicle incorporating a vehicle seat sanitizing system in accordance with embodiments described herein.

FIG. 1 is a block schematic diagram of a vehicle 100 incorporating an autonomous vehicle seat sanitizing system in accordance with embodiments described herein. As used herein, a "vehicle" is any form of motorized transport. In one or more implementations, the vehicle 100 is a conventional passenger vehicle. Various operations of the vehicle may be controlled by a processor(s) 110 and/or a memory 112 including one or more specialized modules as described herein. While arrangements will be described herein with respect to passenger vehicles, it will be understood that embodiments are not limited to passenger vehicles. In some implementations, the vehicle 100 may be any form of motorized transport that benefits from the functionality discussed herein.

The vehicle 100 also includes various elements. It will be understood that in various embodiments it may not be necessary for the vehicle 100 to have all of the elements shown in FIG. 1. The vehicle 100 can have any combination of the various elements shown in FIG. 1. Further, the vehicle 100 can have additional elements to those shown in FIG. 1. In some arrangements, the vehicle 100 may be implemented without one or more of the elements shown in FIG. 1. While the various elements are shown as being located within the vehicle 100 in FIG. 1, it will be understood that one or more of these elements can be located external to the vehicle 100.

Some of the possible elements of the vehicle 100 are shown in FIG. 1 and will be described with reference thereto. Additionally, it will be appreciated that for simplicity and clarity of illustration, where appropriate, reference numerals may have been repeated among the different figures to indicate corresponding or analogous elements. In addition, the discussion outlines numerous specific details to provide a thorough understanding of the embodiments described herein. Those of skill in the art, however, will understand that the embodiments described herein may be practiced using various combinations of these elements.

The vehicle 100 can include one or more processors 110. In one or more arrangements, the processor(s) 110 can be a main processor(s) of the vehicle 100. For instance, the processor(s) 110 can be an electronic control unit (ECU) for the vehicle. The vehicle 100 can include one or more data stores 115 for storing one or more types of data. The data store(s) 115 can include volatile and/or non-volatile memory. Examples of suitable data store(s) 115 include RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The data store(s) 115 can be a component of the processor(s) 110, or the data store(s) 115 can be operably connected to the processor(s) 110 for use thereby. The term "operably connected," as used throughout this description, can include direct or indirect connections, including connections without direct physical contact.

The data store(s) 115 can include sensor data 119. In this context, "sensor data" means any information about the sensors that the vehicle 100 is equipped with, including the capabilities and other information about such sensors. As will be explained below, the vehicle 100 can include the sensor system 120. The sensor data 119 can relate to one or more sensors of the sensor system 120. As an example, in one or more arrangements, the sensor data 119 can include information on one or more vehicle door handle sensors 126 of the sensor system 120.

As noted above, the vehicle 100 can include the sensor system 120. The sensor system 120 can include one or more sensors. "Sensor" means any device, component and/or system that can detect, and/or sense something. The one or more sensors can be configured to detect, and/or sense in real-time. As used herein, the term "real-time" means a level of processing responsiveness that a user or system senses as sufficiently immediate for a particular process or determination to be made, or that enables the processor to keep up with some external process. In arrangements in which the sensor system 120 includes a plurality of sensors, the sensors can work independently from each other. Alternatively, two or more of the sensors can work in combination with each other. In such case, the two or more sensors can form a sensor network. The sensor system 120 and/or the one or more sensors can be operably connected to the processor(s) 110, the data store(s) 115, and/or other element(s) of the vehicle 100 (including any of the elements shown in FIG. 1).

The sensor system 120 can include any suitable type of sensor. However, it will be understood that the embodiments are not limited to the particular sensors described. Various examples of sensors of the sensor system 120 are described herein. The example sensors may be part of the one or more environment sensors 122 and/or the one or more vehicle sensors 121. However, it will be understood that the embodiments are not limited to the particular sensors described. The sensor system 120 may include any sensors suitable for and/or required to enable performance any of the data acquisition and/or vehicle control operations contemplated herein.

Sensors of sensor system 120 may be communicably coupled to the various systems and components of the vehicle 100. Sensor system 120 may include sensors configured to detect the current state or status of vehicle systems and components and to generate signals or other indications regarding the statuses of vehicle systems and components.

The sensor system 120 can include one or more vehicle sensors 121. The vehicle sensor(s) 121 can detect, determine, and/or sense information about the vehicle 100 itself and/or any occupants inside the vehicle.

The vehicle sensor(s) 121 may include occupant sensors 125 configured to detect conditions and/or events inside the vehicle interior or occupant compartment. The occupant sensors 125 may be configured to detect the presence, location(s) and/or number of people or animals (i.e., pets) in the vehicle occupant compartment. Occupant sensors 125 may include seat sensors configured to detect the presence of people, animals, and/or other objects in specific seat(s) in the occupant compartment. Occupant sensors 125 may be configured to detect movement of occupants within the occupant compartment and to detect ingress and egress of occupants from the occupant compartment. Any type of occupant sensor may be used, or several types may be used simultaneously for redundancy. Examples of types of occupant sensors include seat weight sensors, radar sensors, ultrasonic sensors, sonar sensors, etc.

The vehicle sensor(s) 121 may include a door latch sensor 152 operably coupled to each vehicle door and configured to detect whether the door is latched or unlatched. This may determine an "open" or "closed" status of the door (i.e., a vehicle door may be considered open when the door is unlatched and closed when the door is latched).

The sensor system 120 can include one or more environment sensors 122 configured to acquire data of at least a portion of the external environment of the vehicle 100 (e.g., nearby objects). The environment sensors 122 may detect data or information about the external environment in which the vehicle is located or one or more portions thereof. In one or more arrangements, the environment sensors 122 can include one or more radar sensors, one or more LIDAR sensors, one or more cameras, and/or other types of sensors.

The environment sensors 122 may include a door handle sensor 126 operably coupled to each vehicle door handle and configured to detect a proximity or distance of a person to the door handle. The door handle sensors 126 may also be used to determine that a person is opening the door from the outside of the vehicle. In one or more arrangements, the door handle sensors 126 may also be used to determine that a person is approaching a car or moving away from the car by detecting that a distance of the person from the car is either decreasing or increasing. Alternatively, other sensors may be used to perform this function. In one or more arrangements, the door handle sensors 126 may also be used to determine the distance(s) of one or more people from the vehicle. Specifically, data from the door handle sensors 126 may be compared to determine a shortest distance from a person in the vicinity of the vehicle to any door handle. This shortest distance may then be taken as the distance of the person from the vehicle. The door handle sensors 126 may also be used to determine the side(s) of the vehicle on which one or more people are approaching the vehicle. Alternatively, other sensors may be used to perform this distance determination function. The door handle sensors 126 may be any suitable type of sensors, for example, radar, sonar, ultrasonic, etc.

The vehicle wireless communications interface 169 may be configured to enable and/or facilitate communication between the components and systems of the vehicle 100 and entities (such as cloud facilities, cellular and other mobile communications devices, other vehicles, remote servers, pedestrians, etc.) exterior of the vehicle. Wireless communications interface 169 may be configured to facilitate, establish, maintain, and end wireless V2V and V2X communications with any extra-vehicular entity, for example other connectibly-configured vehicles and connected vehicles, pedestrians, servers and entities located in the cloud, edge servers, and other information sources and entities. Information such as sensor data and other types of information may be transmitted and received via the communications interface 169. If required, wireless communications interface 169 may incorporate or be in communication with any network interfaces needed to communicate with any extra-vehicular entities and/or networks. The wireless communications interface may be configured to enable wireless communication between a user mobile device and a vehicle seat sanitizing system control module 124 as described herein, to enable operating commands to be sent remotely to the vehicle seat sanitizing system.

The vehicle 100 can include an input system 130. An "input system" includes any device, component, system, element or arrangement or groups thereof that enable information/data to be entered into a machine. For example, the input system 130 may include a keypad, a touch screen or other interactive display, a voice-recognition system and/or any other device or system which facilitates communications between a user and the vehicle. The input system 130 can receive an input from a vehicle occupant (e.g., a driver or a passenger) or a user located remotely from the vehicle 100, for example, using a mobile device. The vehicle 100 can also include an output system 135. An "output system" includes any device, component, or arrangement or groups thereof that enable information/data to be presented to a vehicle occupant (e.g., a driver, a vehicle passenger, etc.) or a remote user. The input and output systems may enable a user to interact with the vehicle seat sanitizing system as described herein.

The vehicle 100 can include one or more vehicle systems, collectively designated 140. Various examples of the one or more vehicle systems 140 are described herein. However, the vehicle 100 can include more, fewer, or different vehicle systems. It should be appreciated that although particular vehicle systems are separately defined, each or any of the systems or portions thereof may be otherwise combined or segregated via hardware and/or software within the vehicle 100. The vehicle systems 140 can include any or all of a variety of systems usually incorporated into a conventional passenger vehicle, for example, a propulsion system, a braking system, a steering system, throttle system, a suspension system, a transmission system, and/or a navigation system. Each of these systems can include one or more devices, components, and/or a combination thereof, now known or later developed.

The vehicle 100 can include one or more actuators 150. The actuators 150 can be any element or combination of elements operable to modify, adjust and/or alter one or more of the vehicle systems 140 or components thereof to responsive to receiving signals or other inputs from the processor(s) 110, any of the modules stored in memory 112, and/or any other vehicle components or systems. Any suitable actuator can be used. For instance, the one or more actuators 150 can include motors, pneumatic actuators, hydraulic pistons, relays, solenoids, and/or piezoelectric actuators, just to name a few possibilities.

Figure 2:
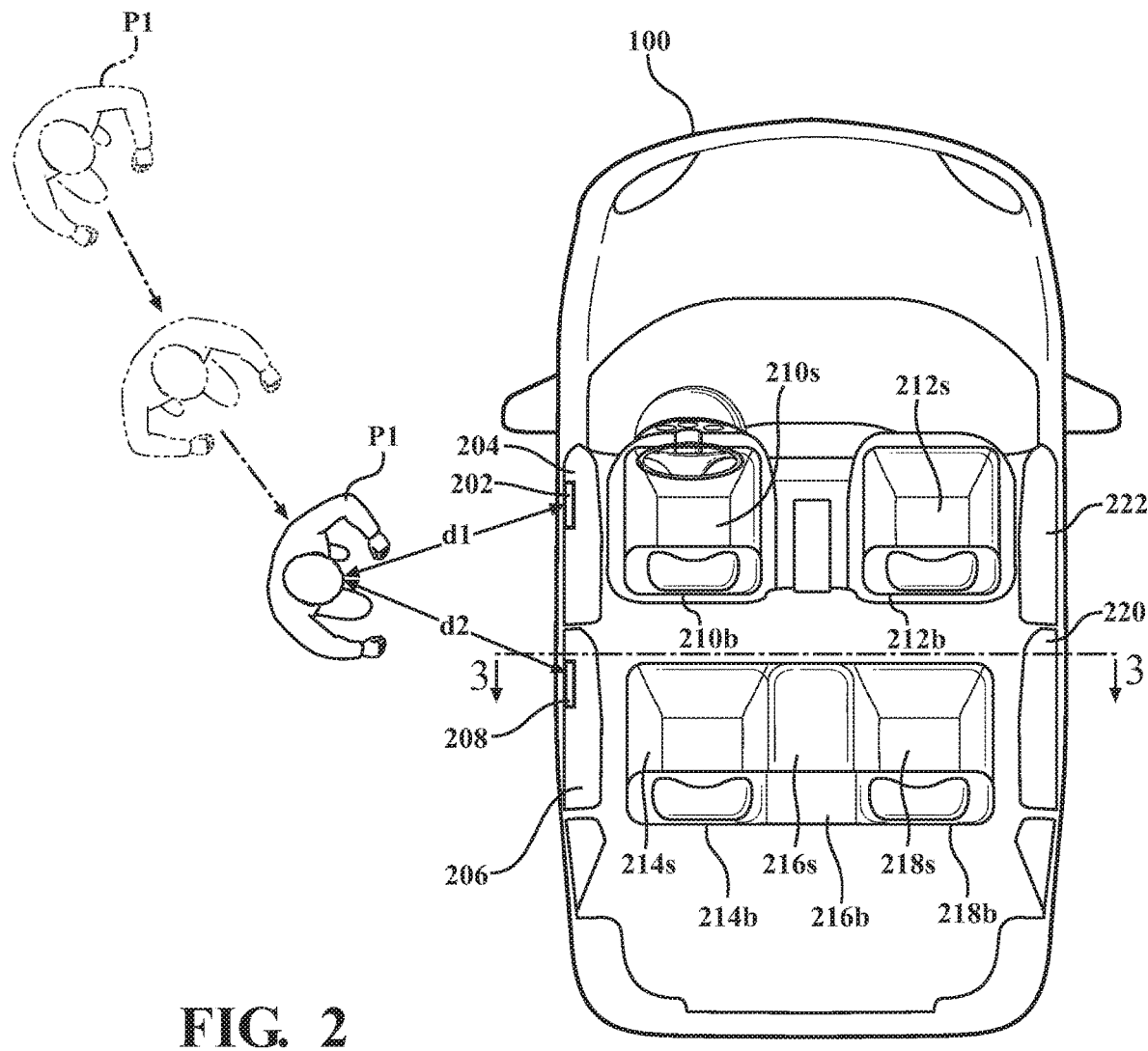
FIG. 2 is a schematic diagram showing a possible arrangement of seats in a vehicle incorporating an embodiment of the vehicle seat sanitizing system.
Figure 3:
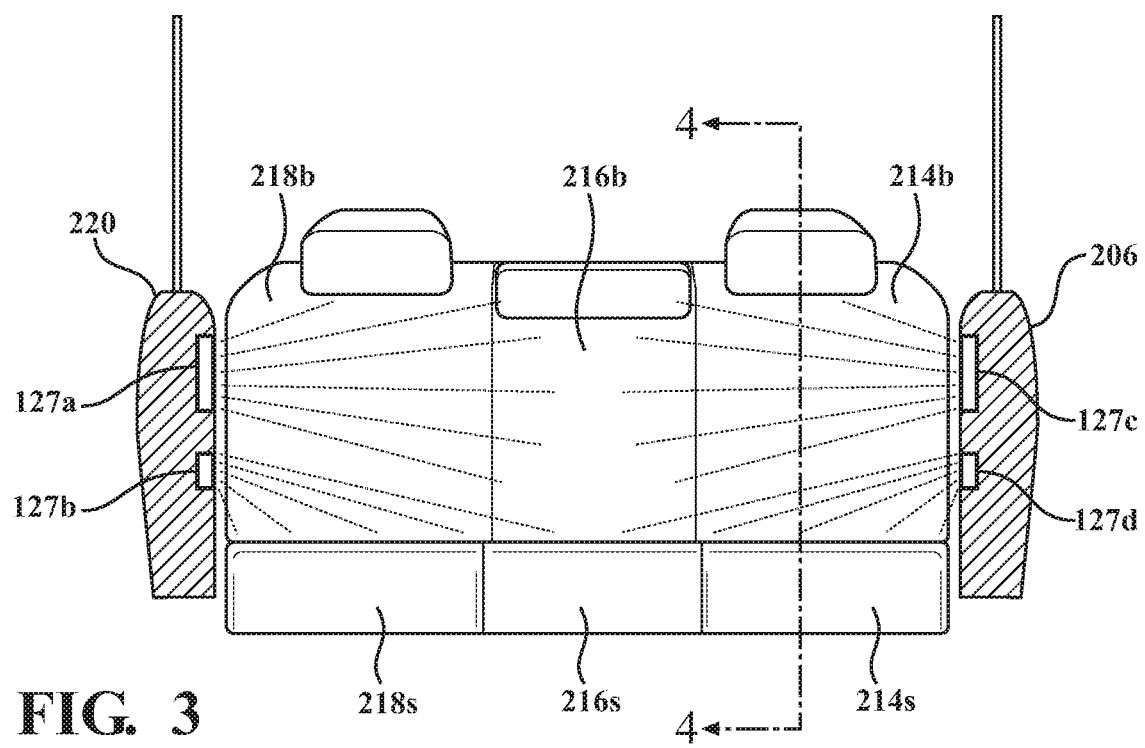
FIG. 3 is a schematic front view of the rear seats of the vehicle of FIG. 2, showing operation of one possible arrangement of UV lights to sanitize the rear seats.
Figure 4:
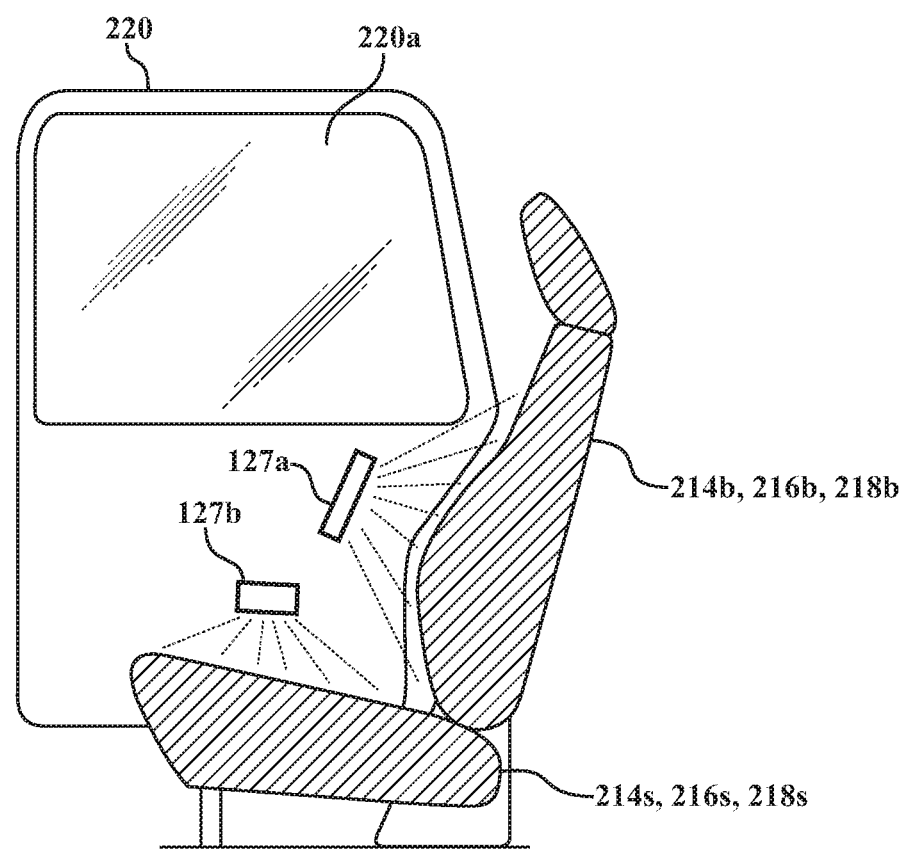
FIG. 4 is a schematic side view of the rear seats of FIG. 3.

The vehicle 100 may include a conventional arrangement of vehicle seats as shown in FIGS. 2-4. However, other arrangements are possible. In the arrangement shown, vehicle 100 has a driver seat 210 with a driver seat bottom 210*s* and a driver seat back 210*b*. A front passenger seat 212 has a front passenger seat bottom 212*s* and a front passenger seat back 212*b*. A rear left passenger seat 214 has a rear left passenger seat bottom 214*s* and a rear left passenger seat back 214*b*. A rear middle passenger seat 216 has a rear middle passenger seat bottom 216*s* and a rear middle passenger seat back 216*b*. A rear right passenger seat 218 has a rear right passenger seat bottom 218*s* and a rear right passenger seat back 218*b*. In the various operational modes described herein, the various seat bottoms and seat backs may be subjected to a sanitizing ultraviolet (UV) light to sanitize the seats before and after use.

The UV light sources 127 may be mounted in the vehicle side doors below the levels of the respective windows. The light sources may be configured to point downwardly and/or rearwardly at one or more angles toward a vehicle seat. In one or more arrangements, each light source may include a light directable to shine on a bottom portion of an associated seat and also on a back portion of the associated seat. Alternatively, each light source may include a light directable to shine on the bottom portion of the seat and a separate light directable to shine on the back portion of the seat. For example, as shown in FIG. 4, the light source mounted in right side rear door 220 may include a light source 127*b* directable to shine on the bottom portion 218*s* of the right side rear seat and a separate light source 127*a* directable to shine on the back portion 218*b* of the seat.

Referring to FIGS. 2-4, UV light sources 127 may be mounted in doors of the vehicle and may be configured to shine on portions of the vehicle seats when activated. In the embodiment shown, vehicle 100 may have a light source 127*a* mounted in a right rear door 220 and configured to shine on a right rear seat back 218*b*. A light source 127*b* may be mounted in the right rear door 220 and may be configured to shine on right rear seat bottom 218*s*. A light source 127*c* may be mounted in the left rear door 206 and may be configured to shine on left rear seat back 214*b*. A light source 127*d* may be mounted in the left rear door 206 and may be configured to shine on left rear seat bottom 214*s*. A light source 127*e* may be mounted in the left front door 204 and may be configured to shine on driver seat back 210*b*. A light source 127*f* may be mounted in the left front door 204 and may be configured to shine on driver seat bottom 210*s*. A light source 127*g* may be mounted in the right front door 222 and may be configured to shine on passenger seat back 212*b*. A light source 127*h* may be mounted in the right front door 222 and may be configured to shine on passenger seat bottom 212*s*.

In particular arrangements, an ultraviolet light source may be configured to selectively direct a sanitizing ultraviolet light onto either of a first seat bottom adjacent the vehicle door or onto a second seat bottom adjacent the first seat bottom. For example, referring to FIGS. 3 and 4, light source 127*b* mounted in rear right door 220 may be configured to selectively direct a sanitizing ultraviolet light onto either of the rear right side seat bottom 218*s* adjacent the rear right vehicle door 220, or onto the rear middle seat bottom 216*s* adjacent the rear right seat bottom 218*s*. Similarly, a left door light source 127*d* may be configured to selectively direct a sanitizing ultraviolet light onto either of the rear left side seat bottom 214*s* adjacent the rear left vehicle door 206, or onto the rear middle seat bottom 216*s* adjacent the rear left seat bottom 214*s*. These arrangements enable door-mounted UV lights to reach and sanitize respective portions of the rear middle seat bottom 216s.

In particular arrangements, light source 127b may be configured to direct a sanitizing ultraviolet light onto both of the rear right seat bottom 218s and the rear middle seat bottom 216s simultaneously. The left side light source 127d may be similarly configured to reach the rear left rear seat bottom and the rear middle seat bottom simultaneously.

In particular arrangements, an ultraviolet light source may be configured to selectively direct a sanitizing ultraviolet light onto either of a first seat back adjacent the vehicle door or onto a second seat back adjacent the first seat back. For example, referring to FIGS. 3 and 4, light source 127a may be configured to selectively direct a sanitizing ultraviolet light onto either of the rear right side seat back 218b adjacent the rear right vehicle door 220, or onto the rear middle seat back 216b adjacent the rear right seat back 218b. Similarly, left door light source 127c may be configured to selectively direct a sanitizing ultraviolet light onto either of the rear left side seat back 214b adjacent the rear left vehicle door 206, or onto the rear middle seat back 216b adjacent the rear left seat back 214b. These arrangements enable door-mounted UV lights to reach and sanitize respective portions of the rear middle seat back 216b.

In particular arrangements, light source 127a may be configured to direct a sanitizing ultraviolet light onto both of the rear right seat back 218b and the rear middle seat back 216b simultaneously. The left side light source 127c may be similarly configured to reach the rear left rear seat back and the rear middle seat back simultaneously.

In one or more arrangements, the UV light source may be configured to emit far-UVC light. As used herein, the term "far-UVC light" refers to UV light having a wavelength of around 220 nm. Such light penetrates biological material only to a very shallow depth, so that it does not penetrate the dead-cell layers at the surface of human skin and does not penetrate the outer surface of the human eye.

The vehicle 100 can include one or more modules, at least some of which are described herein. The modules can be implemented as computer-readable program code that, when executed by processor(s) 110, implement one or more of the various processes described herein. One or more of the modules can be a component of the processor(s) 110, or one or more of the modules can be executed on and/or distributed among other processing systems to which the processor(s) 110 is operably connected. The modules can include instructions (e.g., program logic) executable by one or more processor(s) 110. Alternatively, or in addition, one or more of data store(s) 115 or another portion of the vehicle 100 may contain such instructions.

Generally, a module, as used herein, includes routines, programs, objects, components, data structures, and so on that perform particular tasks or implement particular data types. In further aspects, a memory generally stores the noted modules. The memory associated with a module may be a buffer or cache embedded within a processor, a RAM, a ROM, a flash memory, or another suitable electronic storage medium. In still further aspects, a module as envisioned by the present disclosure is implemented as an application-specific integrated circuit (ASIC), a hardware component of a system on a chip (SoC), as a programmable logic array (PLA), or as another suitable hardware component that is embedded with a defined configuration set (e.g., instructions) for performing the disclosed functions.

In one or more arrangements, one or more of the modules described herein can include artificial or computational intelligence elements, e.g., neural network, fuzzy logic or other machine learning algorithms. Further, in one or more arrangements, one or more of the modules can be distributed among a plurality of the modules described herein. In one or more arrangements, two or more of the modules described herein can be combined into a single module. The module(s) described herein may be partially or fully autonomous and can be operably connected to communicate with each other and with the other elements of the vehicle, including various vehicle systems 140 and/or individual components thereof.

Referring to FIG. 1, embodiments of the vehicle seat sanitizing system described herein may include a vehicle seat sanitizing system control module 124 configured to control autonomous operation of the vehicle seat sanitizing system. In embodiments described herein, a memory 112 may be communicably coupled to the processor(s) 110 and may store the vehicle seat sanitizing system control module 124. The memory may also store other modules 123 for controlling other aspects of vehicle operations. The memory 112 is a random-access memory (RAM), read-only memory (ROM), a hard-disk drive, a flash memory, or other suitable memory for storing the module(s) 123, 124. The module(s) 123, 124 are, for example, computer-readable instructions that when executed by the processor 110, cause the processor(s) 110 to perform the various functions disclosed herein.

Operation of embodiment(s) of the autonomous seat sanitizing system will now be described with reference to FIGS. 5-7.

Figure 5:
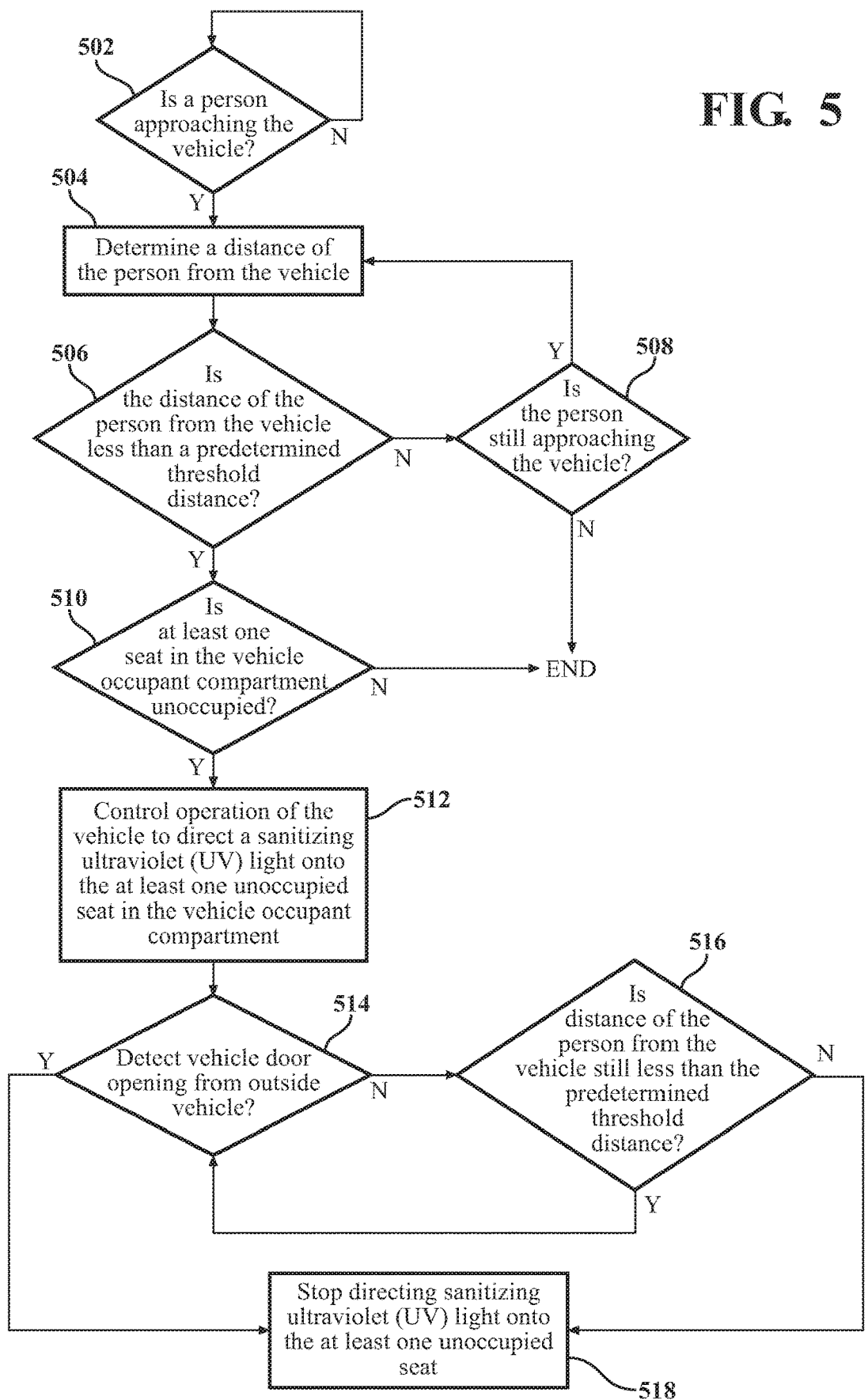
FIG. 5 is a flow diagram illustrating one possible operational mode of an embodiment of the vehicle seat sanitizing system.

Referring to FIG. 5, the seat sanitizing system control module 124 may be configured to detect a person approaching a vehicle. As soon as the approaching person is within a predetermined distance from the vehicle, a sanitizing UV light may be directed onto at least one unoccupied vehicle seat inside the occupant compartment. This control scheme allows for a UV light to be directed onto an empty seat for as long as possible.

In one or more arrangements, the seat sanitizing system control module 124 may include computer-readable instructions that when executed by the processor(s) 110 cause the processor(s) to (in block 502) detect a person approaching the vehicle. FIG. 2 shows an example of a person P1 approaching the vehicle 100. A person may be determined to approaching the vehicle 100 when the distance between the person and the vehicle 100 is detected to be constantly decreasing. While the system is active, the system may constantly monitor the vehicle exterior environment for a person approaching the vehicle. Determinations by the module 124 as described herein may be performed by interpreting and/or receiving information from one or more of the vehicle sensors 121 and/or the environment sensors 122.

In particular arrangements, the seat sanitizing system control module 124 may be configured to detect the person P1 approaching the vehicle 100 using a positioning signal transmitted by a user device carried by the person, and also to determine the distance of the person from the vehicle using the positioning signal. For performance of these functions, the seat sanitizing system control module 124 may operate in communication with the vehicle communications interface 169, for example. Responsive to detection of the person P1 approaching the vehicle 100, the sanitizing system control module 124 may (in block 504) determine a distance of the approaching person P1 from the vehicle.

The sanitizing system control module may then (in block 506) compare the distance of the person P1 from the vehicle 100 to a predetermined threshold distance. The sanitizing system control module 124 may, if the distance of the person P1 from the vehicle 100 is not less than the predetermined threshold distance, determine (in block 508) if the person P1 is still approaching the vehicle 100. For example, the person may be stationary or moving away from the vehicle. If the person P1 is not still approaching the vehicle 100, the module 124 may end the control routine (i.e., since a person who may have entered the vehicle is no longer approaching the vehicle, UV exposure of a vehicle seat may not be needed). If the person starts moving again toward the vehicle or another person starts to move toward the vehicle, control may pass back to block 502 if the system is still active. However, if the person is still approaching the vehicle, control may transfer back to block 504 to determine the distance of the approaching person from the vehicle. The cycle just described may be repeated until the distance of the person from the vehicle is less than the predetermined threshold distance.

Referring back to block 506, when the distance of the person P1 from the vehicle is less than the predetermined threshold distance, the module 124 may (in block 510) determine if at least one seat in the vehicle occupant compartment is unoccupied. If at least one front seat in the vehicle occupant compartment is not unoccupied, the module 124 may end the control routine so that UV light is not applied to an occupied seat. However, if at least one seat in the vehicle occupant compartment was determined to be unoccupied, the sanitizing system control module 124 may control operation of the vehicle 100 to direct a sanitizing ultraviolet (UV) light onto the at least one unoccupied seat. UV light may continue to be directed on the at least one unoccupied seat until a vehicle door is opened from an exterior of the vehicle (block 514), or until the distance of the person from the vehicle is no longer less than the predetermined threshold distance (block 516). If either of these conditions apply, application of the UV light may be discontinued (block 518).

In another operational mode, the sanitizing system control module may include computer-readable instructions that when executed by the one or more processors cause the one or more processors to determine a side of the vehicle along which the person P1 is approaching the vehicle 100. This may be done using the door handle sensors 126. The seat sanitizing system control module 124 may then determine if at least one vehicle seat residing along the side of the vehicle on which the person is approaching the vehicle is unoccupied. For example, if the person is approaching the vehicle along the right side, the module 124 may determine if at least one of the front right passenger seat 212 or the rear right passenger seat 218 is unoccupied. The module may then, if at least one vehicle seat along the side of the vehicle on which the person is approaching is unoccupied, direct the sanitizing ultraviolet light onto the at least one unoccupied vehicle seat.

Figure 6:
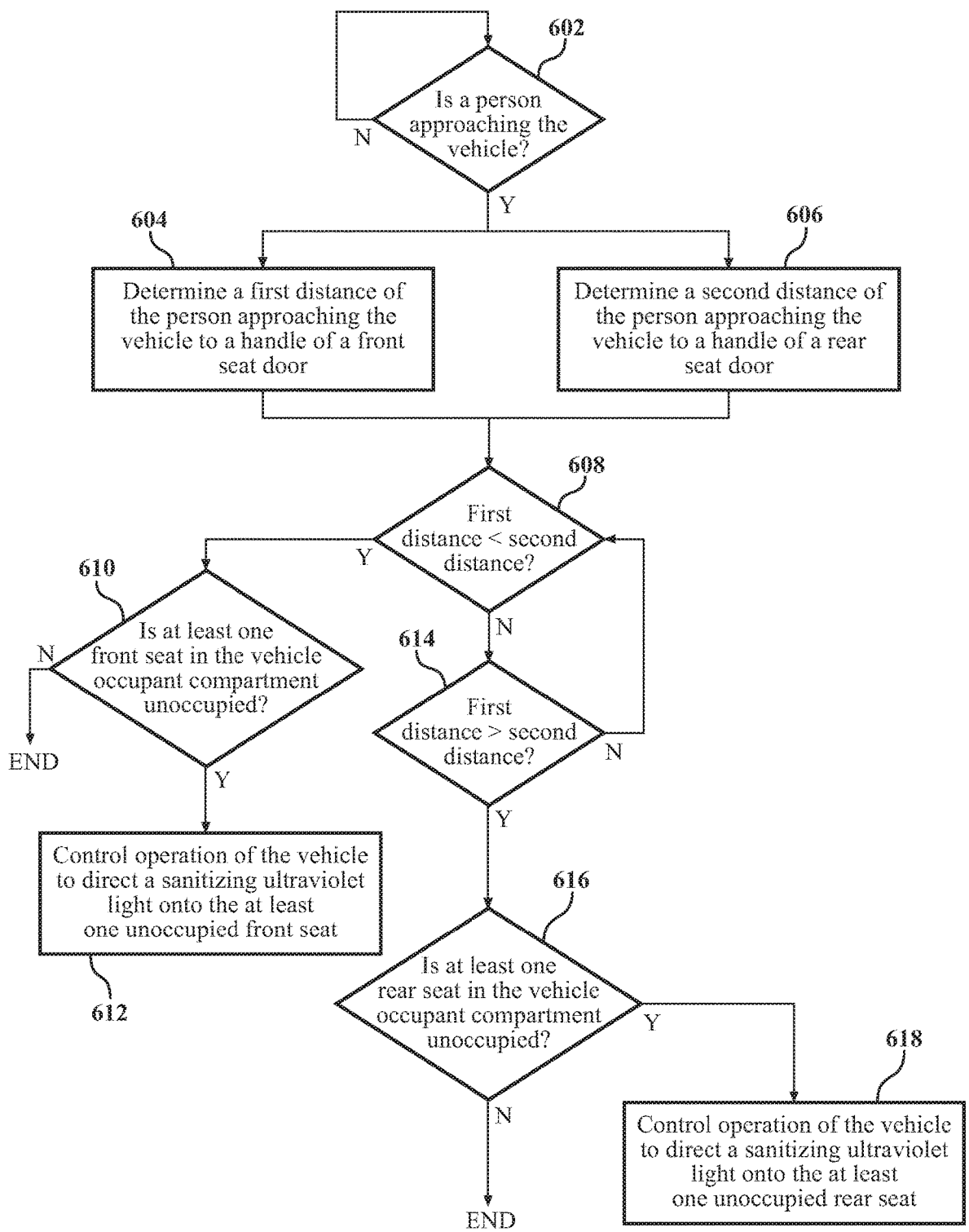
FIG. 6 is a flow diagram illustrating another possible operational mode of an embodiment of the vehicle seat sanitizing system.

FIG. 6 illustrates another operational mode. In this mode, the sanitizing system control module 124 may estimate whether the approaching person will enter the vehicle to occupy a front seat or a rear seat. When this is determined, a UV light may be shined onto any empty front or rear seat to sanitize it for the person prior to the person entering the vehicle.

Referring to FIG. 6, the sanitizing system control module 124 may include computer-readable instructions that when executed by the processor(s) 110 cause the processor(s) to (in block 602) detect a person approaching the vehicle. The sanitizing system control module 124 may then (in block 604), responsive to detection of a person approaching the vehicle, determine a first distance of the person approaching the vehicle to a handle of a front seat door. The module may also (in block 606) determine a second distance of the person approaching the vehicle to a handle of a rear seat door. The module may then (in block 608) compare the first distance to the second distance. The sanitizing system control module may be configured to, if the first distance is less than the second distance, determine (in block 610) if at least one front seat in the vehicle occupant compartment is unoccupied. If at least one front seat in the vehicle occupant compartment is not unoccupied, the module 124 may end the control routine so that UV light is not applied to an occupied seat. However, if at least one front seat in the vehicle occupant compartment is unoccupied, the sanitizing system control module may (in block 612) control operation of the vehicle to direct a sanitizing ultraviolet light onto the at least one unoccupied front seat. In particular arrangements, the sanitizing system control module 124 may be configured to, if the first distance is less than the second distance, control operation of the vehicle to direct a sanitizing ultraviolet light onto all unoccupied front seats in the vehicle occupant compartment.

Referring back to block 614, the sanitizing system control module may also be configured to, if the second distance is less than the first distance, determine (in block 616) if at least one rear seat in the vehicle occupant compartment is unoccupied. If at least one rear seat in the vehicle occupant compartment is not unoccupied, the module 124 may end the control routine so that UV light is not applied to an occupied seat. However, if at least one rear seat in the vehicle occupant compartment is unoccupied, the module may (in block 618) control operation of the vehicle to direct a sanitizing ultraviolet light onto the at least one unoccupied rear seat. In particular arrangements, the sanitizing system control module 124 may be configured to, if the second distance is less than the first distance, control operation of the vehicle to direct a sanitizing ultraviolet light onto all unoccupied rear seats in the vehicle occupant compartment. Referring back to block 608, the module 124 may continue to test the distance of the person from the door handles in blocks 608 and 614 until one of the conditions is true. In particular arrangements, a UV light may be directed at either the unoccupied front seat or the unoccupied rear seat either for a predetermined time of until an associated front or rear door of the vehicle is opened from the exterior of the vehicle.

Figure 7:
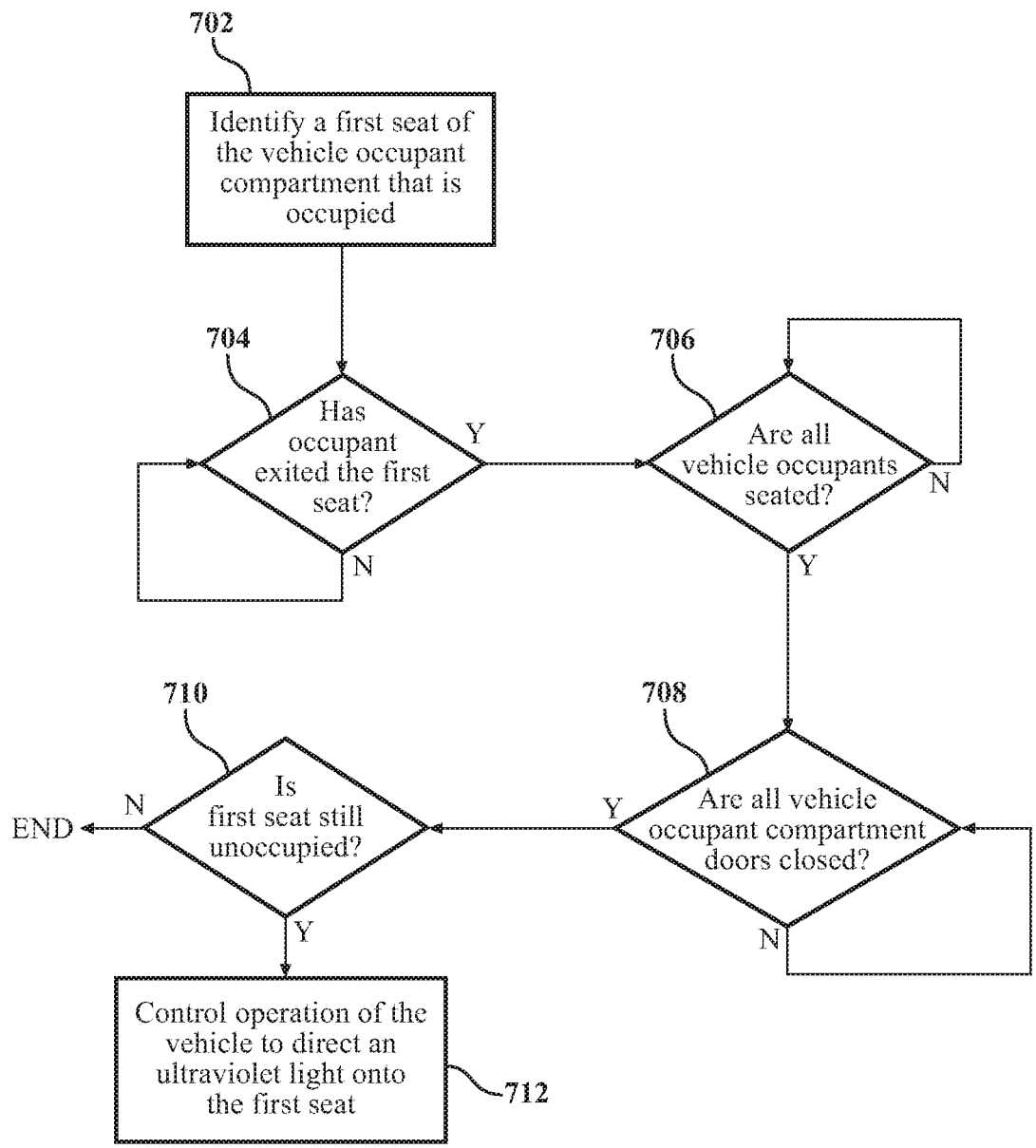
FIG. 7 is a flow diagram illustrating yet another possible operational mode of an embodiment of the vehicle seat sanitizing system.

FIG. 7 illustrates yet another operational mode. In this mode, a recently vacated seat may be detected, and the vehicle may be controlled to direct a UV light onto the recently vacated seat.

Referring to FIG. 7, the sanitizing system control module may include computer-readable instructions that when executed by the processor(s) 110 cause the processor(s) to (in block 702) identify a first seat of the vehicle occupant compartment that is occupied. The sanitizing system control module 124 may then (in block 704) determine when an occupant of the occupied seat leaves the first seat, thereby leaving the first seat unoccupied. After the occupant leaves the first seat, the module may (in block 706) determine when all vehicle occupants are seated. After all vehicle occupants are seated, the module 124 may (in block 708) determine when all vehicle occupant compartment doors are closed. After all vehicle occupant compartment doors are closed, the module may (in block 710) determine if the first (recently vacated) seat is still unoccupied. The module may be configured to, if the first seat is still unoccupied, control (in block 712) operation of the vehicle to direct an ultraviolet light onto the first seat. The steps just described operate to sanitize a seat that has just been vacated.

Detailed embodiments are disclosed herein. However, it is to be understood that the disclosed embodiments are intended only as examples. Therefore, specific structural and functional details disclosed herein are not to be interpreted as limiting, but merely as a basis for the claims and as a representative basis for teaching one skilled in the art to variously employ the aspects herein in virtually any appropriately detailed structure. Further, the terms and phrases used herein are not intended to be limiting but rather to provide an understandable description of possible implementations. Various embodiments are shown in FIGS. 1-7, but the embodiments are not limited to the illustrated structure or application.

The systems, components and/or processes described above can be realized in hardware or a combination of hardware and software and can be realized in a centralized fashion in one processing system or in a distributed fashion where different elements are spread across several interconnected processing systems. Any kind of processing system or another apparatus adapted for carrying out the methods described herein is suited. A typical combination of hardware and software can be a processing system with computer-usable program code that, when being loaded and executed, controls the processing system such that it carries out the methods described herein. The systems, components and/or processes also can be embedded in a computer-readable storage, such as a computer program product or other data programs storage device, readable by a machine, tangibly embodying a program of instructions executable by the machine to perform methods and processes described herein. These elements also can be embedded in an application product which comprises all the features enabling the implementation of the methods described herein and, which when loaded in a processing system, is able to carry out these methods.

Generally, modules as used herein include routines, programs, objects, components, data structures, and so on that perform particular tasks or implement particular data types. In further aspects, a memory generally stores the noted modules. The memory associated with a module may be a buffer or cache embedded within a processor, a RAM, a ROM, a flash memory, or another suitable electronic storage medium. In still further aspects, a module, as envisioned by the present disclosure, is implemented as an application-specific integrated circuit (ASIC), a hardware component of a system on a chip (SoC), as a programmable logic array (PLA), or as another suitable hardware component that is embedded with a defined configuration set (e.g., instructions) for performing the disclosed functions.

Program code embodied on a computer-readable medium may be transmitted using any appropriate medium, including but not limited to wireless, wireline, optical fiber, cable, RF, etc., or any suitable combination of the foregoing. Computer program code for carrying out operations for aspects of the present arrangements may be written in any combination of one or more programming languages, including an object-oriented programming language such as Java™, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The terms "a" and "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The phrase "at least one of . . . and . . . " as used herein refers to and encompasses any and all possible combinations of one or more of the associated listed items. As an example, the phrase "at least one of A, B, and C" includes A only, B only, C only, or any combination thereof (e.g., AB, AC, BC or ABC).

Aspects herein can be embodied in other forms without departing from the spirit or essential attributes thereof. Accordingly, reference should be made to the following claims, rather than to the foregoing specification, as indicating the scope hereof.

What is claimed is:

1. An autonomous seat sanitizing system for a vehicle, the autonomous seat sanitizing system comprising one or more processors and a memory communicably coupled to the one or more processors and storing a vehicle seat sanitizing system control module including computer-readable instructions that when executed by the one or more processors cause the one or more processors to:
   detect a person approaching a vehicle;
   determine a first distance of the person to a handle of a front seat door and a second distance of the person to a handle of a rear seat door;
   if the first distance is less than the second distance, determine if at least one front seat in the vehicle is unoccupied;
   if at least one front seat is unoccupied, control operation of the vehicle to direct a sanitizing ultraviolet light onto the at least one unoccupied front seat;
   if the second distance is less than the first distance, determine if at least one rear seat in the vehicle is unoccupied; and
   if at least one rear seat is unoccupied, control operation of the vehicle to direct a sanitizing ultraviolet light onto the at least one unoccupied rear seat.

2. The autonomous seat sanitizing system of claim 1 wherein the vehicle seat sanitizing system control module includes computer-readable instructions that when executed by the one or more processors cause the one or more processors to:
   detect the person approaching the vehicle using a positioning signal transmitted by a mobile device carried by the person; and
   determine the distance of the person from the vehicle using the positioning signal.

3. The autonomous seat sanitizing system of claim 1 wherein the vehicle seat sanitizing system control module includes computer-readable instructions that when executed by the one or more processors cause the one or more processors to:
   determine a side of the vehicle along which the person is approaching the vehicle;
   determine if at least one vehicle seat residing along the side of the vehicle on which the person is approaching the vehicle is unoccupied; and
   if at least one vehicle seat along the side of the vehicle on which the person is approaching is unoccupied, direct the sanitizing ultraviolet light onto the at least one unoccupied vehicle seat.

4. The autonomous seat sanitizing system of claim 1 wherein the vehicle seat sanitizing system control module includes computer-readable instructions that when executed by the one or more processors cause the one or more processors to:
- if the first distance is less than the second distance, control operation of the vehicle to direct the sanitizing ultraviolet light onto all unoccupied front seats in an occupant compartment of the vehicle; and
- if the second distance is less than the first distance, control operation of the vehicle to direct the sanitizing ultraviolet light onto all unoccupied rear seats in the vehicle occupant compartment.

5. The autonomous seat sanitizing system of claim 1 wherein the vehicle seat sanitizing system control module includes computer-readable instructions that when executed by the one or more processors cause the one or more processors to:
- identify a first seat of an occupant compartment of the vehicle that is occupied;
- determine when an occupant of the occupied first seat leaves the first seat, thereby leaving the first seat unoccupied;
- determine when all vehicle occupants are seated;
- determine when all vehicle occupant compartment doors are closed;
- determine if the first seat is still unoccupied; and
- if the first seat is still unoccupied, control operation of the vehicle to direct the sanitizing ultraviolet light onto the first seat.

6. The autonomous seat sanitizing system of claim 1 wherein the sanitizing ultraviolet light is a far-UVC light.

7. The autonomous seat sanitizing system of claim 1 comprising an ultraviolet light source mounted on a vehicle side door and configured to selectively direct a sanitizing ultraviolet light onto either of a first seat bottom adjacent the vehicle side door or onto a second seat bottom adjacent the first seat bottom.

8. The autonomous seat sanitizing system of claim 7 wherein the ultraviolet light source is configured to direct the sanitizing ultraviolet light onto both of the first seat bottom and the second seat bottom simultaneously.

9. The autonomous seat sanitizing system of claim 1 comprising an ultraviolet light source mounted on a vehicle side door configured to selectively direct a sanitizing ultraviolet light onto either of a first seat back adjacent the vehicle side door or onto a second seat back adjacent the first seat back.

10. The autonomous seat sanitizing system of claim 9 wherein the ultraviolet light source is configured to direct the sanitizing ultraviolet light onto both of the first seat back and the second seat back simultaneously.

* * * * *